United States Patent
Gillespie et al.

(10) Patent No.: US 11,045,775 B2
(45) Date of Patent: Jun. 29, 2021

(54) ACID MIXING SYSTEM

(71) Applicant: Isopure, Corp., Louisville, KY (US)

(72) Inventors: Kevin C. Gillespie, Simpsonville, KY (US); Zachary Patrick Ford, Louisville, KY (US); Guillermo J. Cohen Freue, Bryn Mawr, PA (US)

(73) Assignee: Isopure, Corp., Louisville, KY (US)

( * ) Notice: Subject to any disclaimer, the term of this patent is extended or adjusted under 35 U.S.C. 154(b) by 328 days.

(21) Appl. No.: 15/933,313

(22) Filed: Mar. 22, 2018

(65) Prior Publication Data

US 2019/0060850 A1    Feb. 28, 2019

Related U.S. Application Data

(60) Provisional application No. 62/474,920, filed on Mar. 22, 2017.

(51) Int. Cl.
*B01F 3/12* (2006.01)
*B01F 15/00* (2006.01)
(Continued)

(52) U.S. Cl.
CPC ......... *B01F 3/1271* (2013.01); *A61M 1/1656* (2013.01); *A61M 1/1666* (2014.02); *B01F 1/0022* (2013.01); *B01F 1/0038* (2013.01); *B01F 5/0413* (2013.01); *B01F 5/102* (2013.01); *B01F 5/106* (2013.01); *B01F 15/00162* (2013.01); *B01F 15/00227* (2013.01);
(Continued)

(58) Field of Classification Search
CPC .............. A61M 1/1656; A61M 1/1666; A61M 2205/3317; A61M 2205/3331; A61M 2205/3382; A61M 2205/3592; A61M 2205/502; A61M 2205/6072; B01F 1/0022; B01F 1/0038; B01F 3/1271; B01F 5/102; B01F 5/106
USPC .................................................. 366/136, 137
See application file for complete search history.

(56) References Cited

U.S. PATENT DOCUMENTS

| 3,482,718 A | 12/1969 | Moriarty |
| 3,680,725 A | 8/1972 | Armstrong |

(Continued)

FOREIGN PATENT DOCUMENTS

| CN | 110612155 A | 12/2019 |
| EP | 3600637 | 2/2020 |

(Continued)

OTHER PUBLICATIONS

International Searching Authority: the International Search Report and Written Opinion of PCT Serial No. PCT/US2018/023888; 13 Pages; dated Jun. 20, 2018.

(Continued)

*Primary Examiner* — Tony G Soohoo
(74) *Attorney, Agent, or Firm* — Middleton Reutlinger

(57) ABSTRACT

A system for mixing a liquid with a powder into a solution batch includes a hopper (20) into which said powder is deposited, the hopper (20) having a powder outlet (22) therein. A mix tank (60) is also provided having a liquid supply inlet (62), a recirculation inlet (64), and a solution outlet (66). A mix pump (40) that is in fluid communication with the solution outlet (66), the powder outlet (22), and the recirculation inlet (64) operates to mix and transfer the solution.

19 Claims, 7 Drawing Sheets

(51) Int. Cl.
  *B01F 5/04* (2006.01)
  *A61M 1/16* (2006.01)
  *B01F 5/10* (2006.01)
  *B01F 1/00* (2006.01)
  *B01F 15/02* (2006.01)
  *G01N 9/26* (2006.01)

(52) U.S. Cl.
  CPC .. *B01F 15/00233* (2013.01); *B01F 15/00318* (2013.01); *B01F 15/0235* (2013.01); *A61M 2205/3317* (2013.01); *A61M 2205/3331* (2013.01); *A61M 2205/3382* (2013.01); *A61M 2205/3592* (2013.01); *A61M 2205/502* (2013.01); *A61M 2205/6072* (2013.01); *B01F 2003/125* (2013.01); *B01F 2215/0034* (2013.01); *G01N 9/26* (2013.01)

(56) References Cited

U.S. PATENT DOCUMENTS

| | | | | |
|---|---|---|---|---|
| 3,777,775 | A * | 12/1973 | Handleman | B01F 15/00928 169/14 |
| 4,163,712 | A * | 8/1979 | Smith | B01F 3/04985 210/622 |
| 4,186,772 | A * | 2/1980 | Handleman | A62C 31/12 137/891 |
| 4,863,277 | A * | 9/1989 | Neal | B01F 3/1271 366/137 |
| 5,613,824 | A | 3/1997 | Kato | |
| 5,775,803 | A * | 7/1998 | Montgomery | G05D 21/02 366/152.2 |
| 5,813,192 | A | 9/1998 | White | |
| 5,947,596 | A | 9/1999 | Dowd | |
| 7,275,856 | B2 * | 10/2007 | Koetas | B24D 18/009 366/102 |
| 7,972,055 | B2 | 7/2011 | Adent | A01K 5/02 366/142 |
| 8,091,807 | B2 * | 1/2012 | Kerns | B01F 7/00825 241/20 |
| 8,376,251 | B2 * | 2/2013 | Kerns | B01F 5/104 241/20 |
| 9,527,051 | B2 | 12/2016 | Volker | |
| 9,593,050 | B2 * | 3/2017 | Welker | B28C 5/388 |
| 10,500,326 | B2 | 12/2019 | Gillespie | |
| 10,532,954 | B2 * | 1/2020 | Welker | B28C 7/026 |
| 10,689,302 | B2 * | 6/2020 | Welker | B28C 7/02 |
| 2004/0245124 | A1 | 12/2004 | Hurst | B01F 15/00824 206/219 |
| 2004/0245144 | A1* | 12/2004 | Hurst | B01F 15/00824 206/527 |
| 2006/0076251 | A1* | 4/2006 | Hurst | B01F 13/0818 206/219 |
| 2006/0188412 | A1* | 8/2006 | Takahashi | H01L 21/67253 422/105 |
| 2009/0304463 | A1 | 12/2009 | Dance | |
| 2013/0206876 | A1* | 8/2013 | Kerns | B01F 5/104 241/16 |
| 2014/0044485 | A1* | 2/2014 | Wallace | B01D 61/025 405/36 |
| 2015/0003185 | A1* | 1/2015 | Woodle | B01F 5/0206 366/136 |
| 2016/0107128 | A1 | 4/2016 | Dumschat | |
| 2018/0213819 | A1* | 8/2018 | Jetton | B01F 3/1271 |
| 2018/0361047 | A1 | 12/2018 | Gillespie et al. | |
| 2019/0060850 | A1* | 2/2019 | Gillespie | B01F 15/0235 |
| 2019/0111401 | A1* | 4/2019 | Lucas | E21B 43/26 |
| 2019/0264517 | A1* | 8/2019 | Chong | B01F 13/004 |
| 2019/0358386 | A1* | 11/2019 | Eyrard | A61K 9/08 |

FOREIGN PATENT DOCUMENTS

| | | |
|---|---|---|
| JP | S5019594 | 3/1975 |
| WO | 9211046 | 7/1992 |
| WO | 0074833 | 12/2000 |
| WO | 2004052727 | 6/2004 |
| WO | 2018175811 | 9/2018 |
| WO | 2018237063 A1 | 12/2018 |

OTHER PUBLICATIONS

U.S. Appl. No. 16/705,888, filed Dec. 6, 2019 entitled "Bag Opening System".
Australian Patent App. 2018237375 filed Mar. 22, 2018 (national stage entry date Oct. 21, 2019) entitled "Acid Mixing System".
Canadian Patent App. 3,057,465 (national stage entry date Oct. 11, 2019) filed Mar. 22, 2018 entitled "Acid Mixing System".
Mexican Patent App. MX/a/2019/011300 filed Mar. 22, 2018 (national stage entry date Sep. 23, 2019) entitled "Acid Mixing System".
EPO; Communication Pursuant to Rules 161(1) and 162 EPC in app. No. EP18717774.6 dated Oct. 30, 2019.
ISA; International Search Report and Written Opinion of PCT No. PCT/US2018/038581 dated Sep. 4, 2018.
Australian Patent App. 2018288820 filed Jun. 20, 2018 (national stage entry date Jan. 13, 2020) entitled "Bag Opening System".
European Patent App. 18740049.4 filed Jun. 20, 2018 (national stage entry date Jan. 16, 2020) entitled "Bag Opening System".
Mexican Patent App. MX/a/2019/015711 filed Jun. 20, 2018 (national stage entry date Dec. 19, 2019) entitled "Bag Opening System".
Japanese Patent App. 2019-570395 filed Jun. 20, 2018 (national stage entry date Jan. 12, 2020) entitled "Bag Opening System".
EPO; Communication Pursuant to Rules 161(1) and 162 EPC in app. No. EP18740049.4 dated Jan. 30, 2020.
European Patent Office, Communication pursuant to Article 94(3) EPC dated Nov. 23, 2020 for EP Application No. 18717774.6, 5 pages.
Canadian Intellectual Property Office, Notice of Allowance dated Jan. 5, 2021 for CA Application No. 3,057,465, 1 page.

* cited by examiner

ACID MIXING SYSTEM

FIELD OF THE INVENTION

The present invention relates generally to system for mixing a solution using a liquid and a dry powder and more particularly for accurately and automatically mixing an acid solution for use in a hemodialysis system.

BACKGROUND OF THE INVENTION

There is a need in the medical field for mixing various acidic solutions for a wide variety of medical clinical uses. Many of these solutions are prepared on site by mixing a predetermined dry acid powder with a predetermined volume of water to produce a desired pH acid solution. Most of these prior art acid solution mixing systems require a great deal of laborious and time-consuming handling. For example, a dry powder bag must be opened and a volume of powder must be measured and placed into a suitable mixing container. Then a volume of water must be carefully measured and poured into the container for mixing, either by hand or by a motorized paddle or other mixing instrument.

Once the solution is mixed a portion thereof must be tested to determine that the proper pH or solution concentration has been achieved. If the pH or concentration of the solution is incorrect by even a small amount, the portions must be adjusted and re-mixed, since in medical applications such as hemodialysis even a small variation in pH can have catastrophic results. In these prior art mixing systems, even where some portion of the process is automated, there is a great deal of user-intensive labor required in the mixing process.

Additionally, great care must be taken to avoid storing a mixed solution of a specified concentration in a storage tank that matches that concentration. When transfers of mismatched batches occur, both solution batches are ruined. Even worse, if the error is not caught before the solution is used the results can be catastrophic, particularly in medical system applications.

Thus there is a need in the art for a dry powder and fluid solution mixing system, for example an acid solution mixing system, that minimizes user labor while assuring consistent mixing, quality control, and accurate pH in each batch of solution being prepared.

SUMMARY OF THE INVENTION

Various embodiments and aspects of the invention overcome the aforementioned deficiencies in the prior art by providing generally a system for mixing a solution and more particularly a system for automatically mixing and testing an acid solution to produce a solution having a desired pH or concentration. It should be noted that while the various implementations and embodiments discussed in this specification refer mainly to a system for mixing an acid solution, one of ordinary skill will recognize that the instant system may be utilized to mix any of a wide variety of powders with any of a wide variety of fluids without departing from the scope of the invention. Thus, the system described herein is not limited to the mixing of acid solutions, but rather may be implemented to mix any solution utilizing a powder or dry material and a liquid or fluid.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Before explaining exemplary embodiments consistent with the present disclosure in detail, it is to be understood that the disclosure is not limited in its application to the details of constructions and to the arrangements set forth in the following description or illustrated in the drawings. The disclosure is capable of embodiments in addition to those described and is capable of being practiced and carried out in various ways. Also, it is to be understood that the phraseology and terminology employed herein, as well as in the abstract, are for the purpose of description and should not be regarded as limiting.

In various aspects and embodiments a system for mixing a solution of a dry powder and a fluid includes a hopper having a powder outlet that is in fluid communication with a mix pump line, so that powder may be deposited into the mix pump line and then distributed into a mix tank. The hopper powder outlet may be in fluid communication with a control valve that meters or drops powder into mix pump line.

In some aspects and embodiments the mix tank provides an enclosed area in which the solution is mixed and includes a liquid supply inlet, a recirculation line, and a mix solution outlet. The solution outlet and recirculation line are also in fluid communication with the mix pump to provide continuous mixing of the liquid and powder as the pump recirculates fluid. In further aspects of the invention the mix tank may include a level sensor capable of sensing a level of solution in the mix tank, for example a predetermined volume based on a desired batch. In various aspects and embodiments of the invention a processor or controller is provided, having signal and/or data inputs and signal and/or data outputs for accepting and supplying various electrical signals to and from components of the invention. The controller may include a data memory for storing instructions to operate the various invention components as well as an operator interface or equivalent user input to allow an operator to receive data from the system as well as provide user commands.

In other aspects and embodiments a bar code scanner may be operatively coupled to the controller via an input, to permit an operator to scan a bar code provided on a powder bag or case, thereby inputting data related to that specific powder bag (or batch) for tracking and verification purposes. In some embodiments this feature is useful when mixing solutions for medical uses such as hemodialysis, wherein each quantity of powder input—for example a bag or case of dry acid mix—is tracked by a bar code or similar identifier. In some aspects and embodiments controller stores the information provided so that each batch that is mixed can be tracked by the powder batch number, manufacturer, sale date, and size, to mention some exemplary but non-limiting data that may be stored and tracked.

In various embodiments a batch transfer/recirculation line is provided having an RFID interrogator secured proximate a coupling. The interrogator is operatively coupled to the controller and interrogates a concomitant RFID tag mounted near the inlet of a storage tank where the transfer coupling is secured when transferring a batch to the storage tank. When the RFID interrogator reads data from the RFID tag that indicates the solution in the mix tank is the same as that stored in the storage tank, the system permits the transfer. When the RFID interrogator reads data from the RFID tag that indicates the solution in the mix tank is not the same as that stored in the storage tank, the system prohibits the transfer of the solution and provides an alarm through an operator interface to alert an operator to the error.

The accompanying drawings, which are incorporated and form a part of the specification illustrate exemplary but non-limiting embodiments of the disclosure, and together with the description, serve to explain the principles of the disclosure.

Those skilled in the art will appreciate that the inventive concepts and principles upon which the disclosure is based may readily be utilized as a basis for designing other structures, systems, methods, and articles of manufacture for implementing the purposes of the present disclosure. Accordingly the claims appended hereto should be construed to include such equivalent constructions without departing from the spirit and scope of the invention herein disclosed.

DETAILED DESCRIPTION OF THE PREFERRED EMBODIMENT(S)

Figure 1:
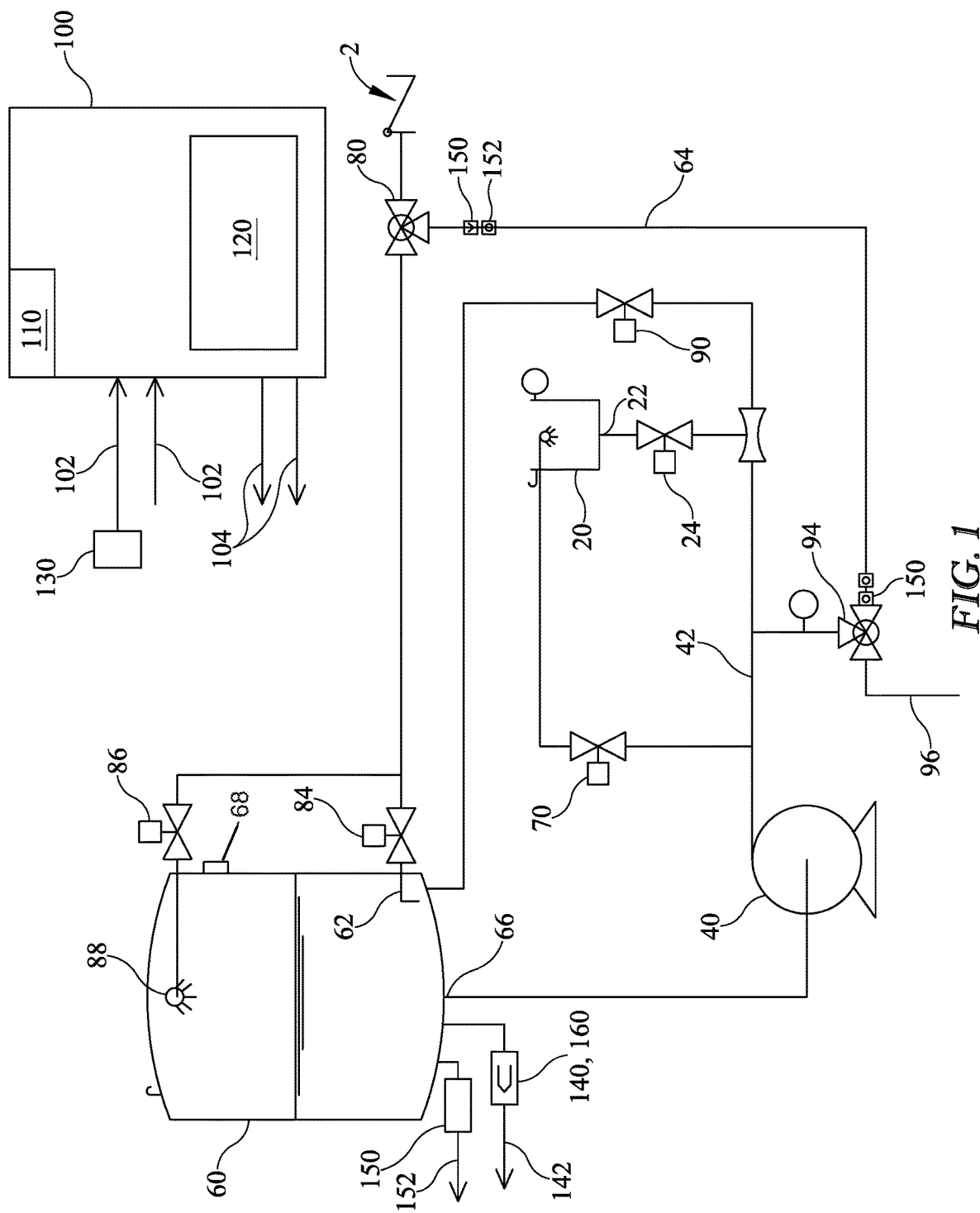
FIG. 1 illustrates an isometric diagram of a mixing system in accordance with one embodiment of the present invention.
Figure 2:
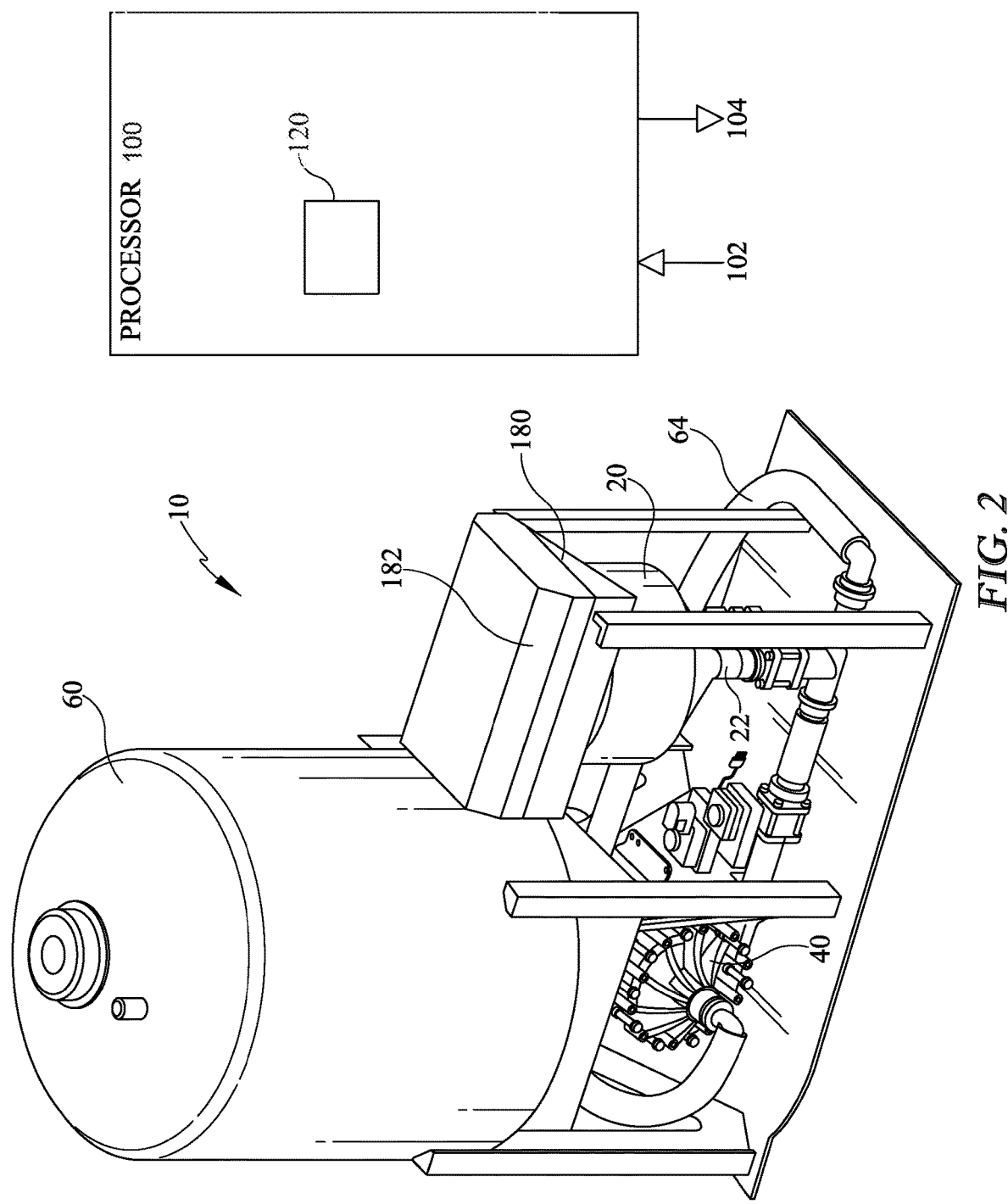
FIG. 2 illustrates an isometric diagram of a mixing system in accordance with one embodiment of the present invention.
Figure 3:
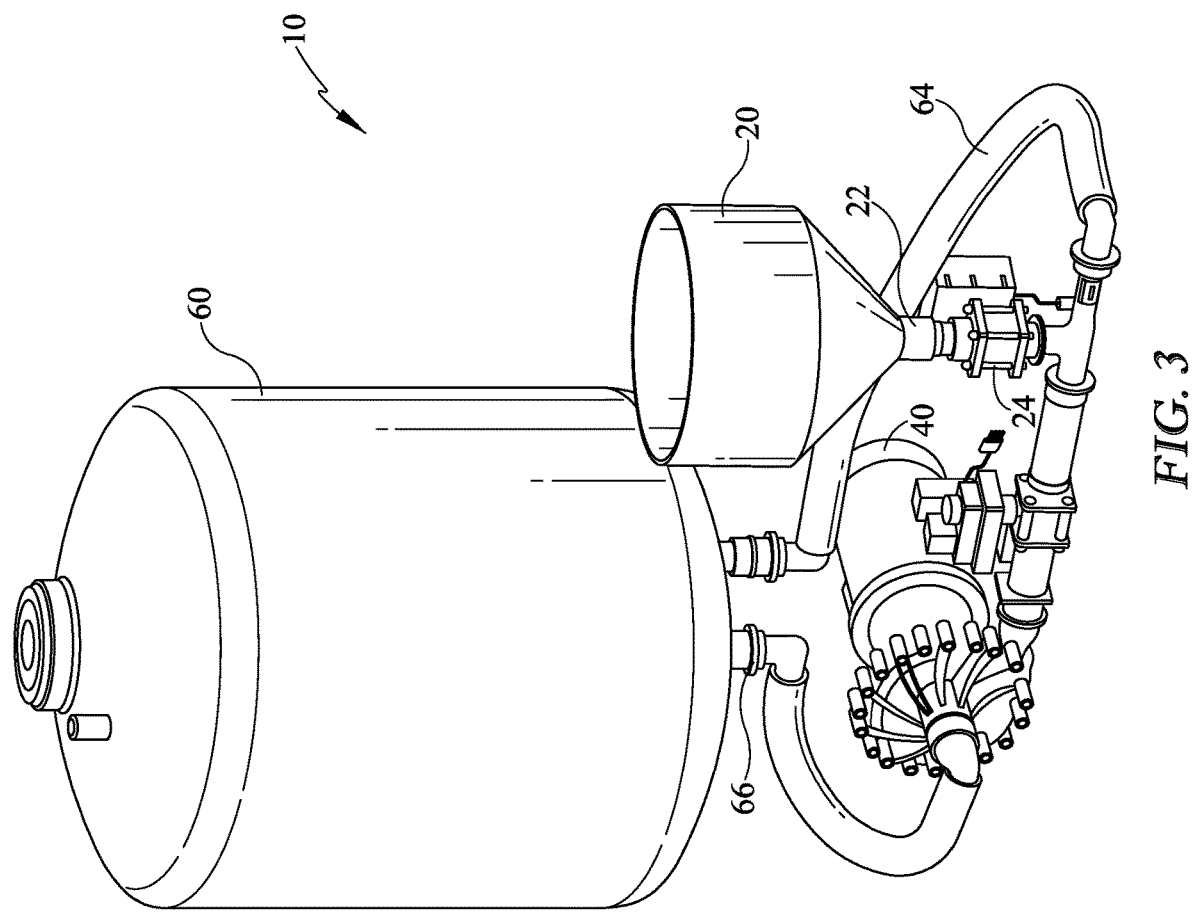
FIG. 3 illustrates an isometric view of a mix tank, hopper, mix pump and piping assembly in accordance with one embodiment of the present invention.
Figure 4:
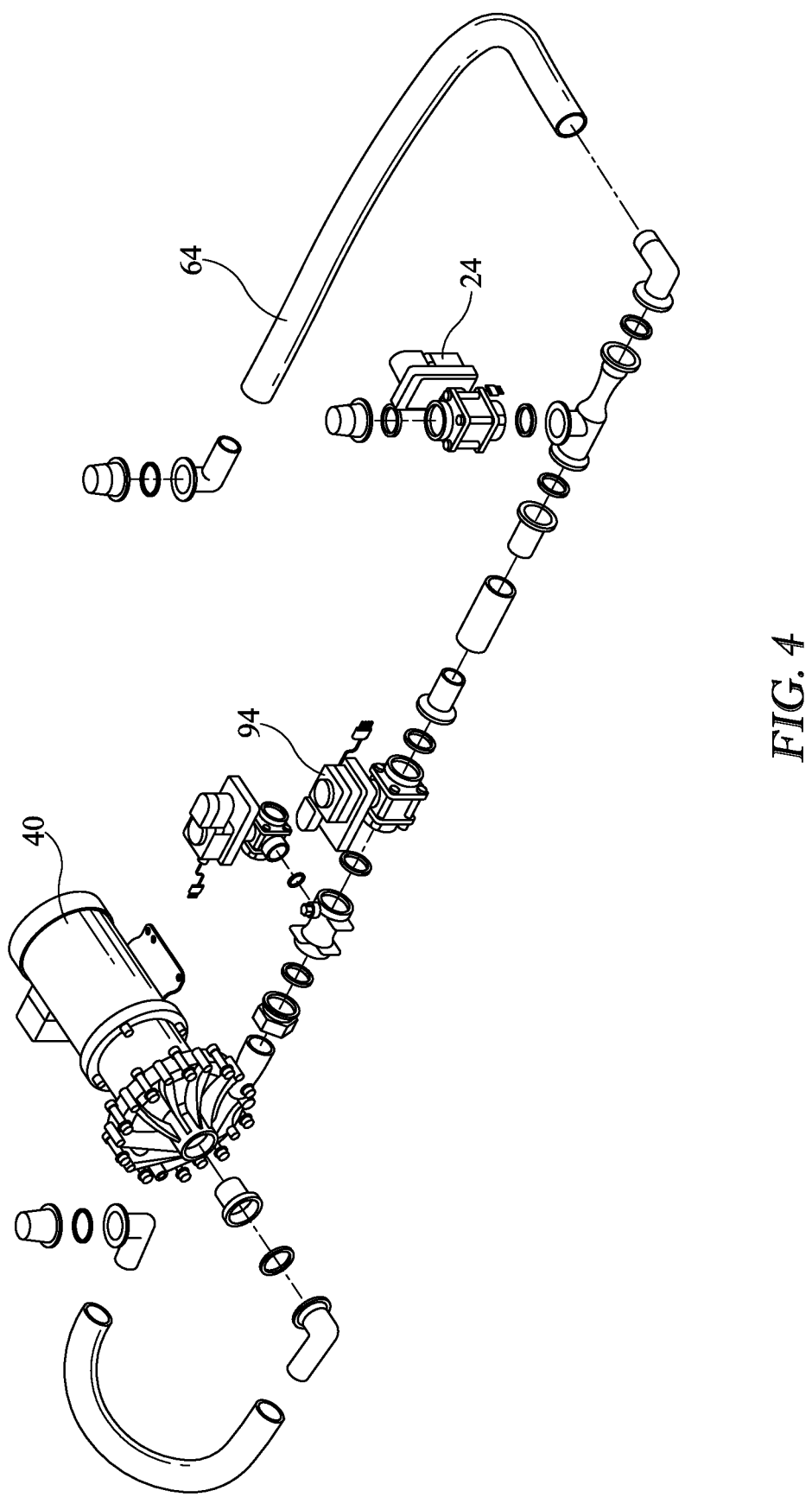
FIG. 4 illustrates an exploded isometric view of a mix pump and piping in accordance with one embodiment of the present invention.
Figure 5:
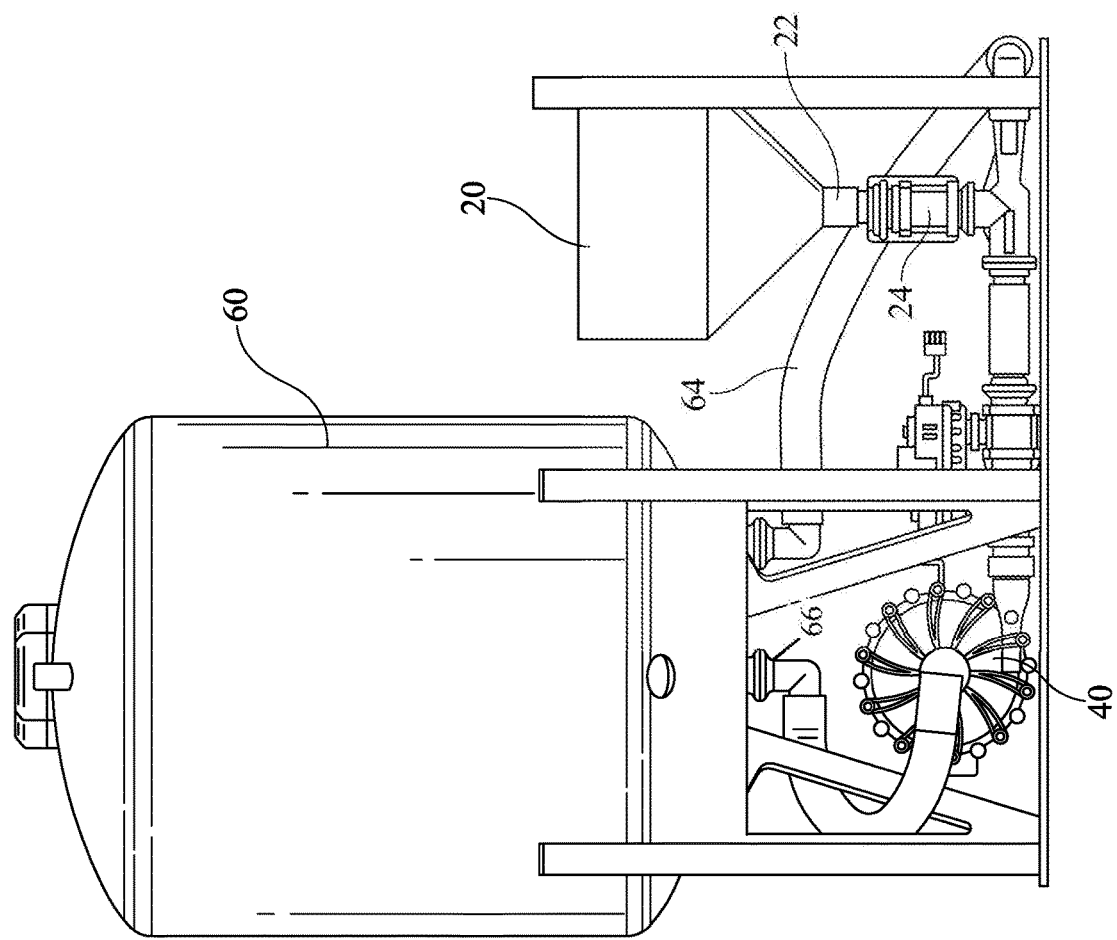
FIG. 5 illustrates an elevation view of a mixing system in accordance with some embodiments of the present invention.

Referring now to the drawing Figures, and in particular FIGS. 1-3, and in accordance with a several aspects and exemplary embodiments of the present invention a mixing system 10 for mixing a powder 1 or dry material and a liquid 2 or fluid into a solution 3 includes a hopper 20 into which the powder 1 may be deposited. The hopper 20 includes a powder outlet 22 that is in fluid communication with a mix pump 40 line 42, such that powder may be deposited in to the mix pump 40 line and then distributed into a mix tank 60. Hopper 20 powder outlet 22 may be in fluid communication with a control valve 24 that meters or drops powder into mix pump line 42, thereby providing for measured powder input to mix tank 60 by operation of pump 40.

Mix tank 60 provides an enclosed area in which the solution 3 is mixed and includes a liquid supply inlet 62, a recirculation line 64, and a mix solution outlet 66. The solution outlet 66 and recirculation line 64 are also in fluid communication with mix pump 40, so that mix pump 40 may provide continuous mixing of the liquid 2 and powder 1 as pump 40 recirculates fluid through pump line 42 and recirculation line 64. In further aspects of the invention mix tank 60 also includes a level sensor 68, or a plurality thereof, capable of sensing a level of solution 3 in mix tank 60 representative of a predetermined volume of solution. Level sensors 68 have an output representative of a fluid level detected that is operatively coupled to an input 102 of controller 100. Thus controller 100 can be provided with instructions to fill mix tank 60 to a specific volume by monitoring level sensors 68, as will be discussed further herein below.

In various aspects and embodiments of the invention as depicted in FIG. 1 a processor 100 or controller is provided, having signal and/or data inputs 102 and signal and/or data outputs 104 for accepting and supplying various electrical signals to and from components of the invention. Controller 100 may include a data memory 110 for storing instructions to operate the various invention components as well as an operator interface 120 or equivalent user input to allow an operator to receive and view data and various system 10 operating parameters as well as provide user commands thereto. Furthermore, in one aspect of the invention, a bar code scanner 130 is operatively coupled to controller 100 via an input 102 thereto, to permit an operator to scan a bar code provided on a powder 1 bag, thereby inputting data related to that specific powder 1 bag (or batch) for tracking and verification purposes. In some embodiments this feature is useful where mixing solutions 3 for medical uses, wherein each quantity of powder 1 input is tracked by a bar code or similar identifier. In some aspects and embodiments controller 100 stores the information provided in each powder 1 bag bar code scanned such that each tank 60 that is mixed can be tracked by the powder 1 batch number, manufacturer, sale date, and size, to mention some exemplary but non-limiting data that may be stored and tracked.

As best seen in FIG. 1 processor 100 inputs 102 and outputs 104 are in some embodiments operatively coupled to various valves disposed throughout system 10. For example a hopper 20 outlet valve 24 is disposed below powder hopper 20 to release powder 1 into mix pump line 42. Hopper outlet valve 24 is operatively coupled to an output 103 of controller 100 to actuate valve 24, and further may include a plurality of operatively coupled signal inputs 102 to controller 100 to indicate an open and/or closed valve 24 position, or a signal input that is indicative of valve 24 position. Each valve herein described may be operatively coupled to controller 100 inputs 102 and outputs 104 so that system 10 may operate each valve individually, and monitor the position of each valve through system 10 operation.

In some aspects and embodiments a mixing jets valve 70 is provided in fluid communication with mix pump line 42 to siphon a portion of the fluid 2 circulated through pump 60 into hopper 20, thereby assuring that all powder 1 placed in hopper 20 is ultimately distributed into mix tank 60 by operation of pump 40. Mixing jets valve 70 is operatively coupled to controller 100 inputs 102 and outputs 104. In some aspects and embodiments of the invention, a water supply inlet valve 80 is operatively coupled to an output 104 of controller 100, such that controller 100 can automatically control the amount of fluid 2 supplied to mix tank 60 according to the programming instructions supplied to the controller 100, as will be discussed further herein below. In other embodiments water supply valve 80 may be a three-way valve that permits process water 1 (or fluid) to enter mix tank 60 or provides a fluid communication path for recirculation line 64 from mix pump 40, depending upon valve 80 position.

In some further aspects and embodiments an input water valve 84 is operatively coupled to controller 100 and is disposed proximate mix tank 60 to regulate fluid 2 flow into tank 60 when required. Additionally, water supply 2 is also in fluid communication with a spray/rinse valve 86 that supplies water to a spray head 88 for rinsing and cleaning mix tank 60 when desired. Spray/rinse valve 86 is also operatively connected to an output 104 of controller 100 so that a rinse cycle may be initiated through user interface 120 when necessary or alternatively automatically performed after each batch of solution is produced and transferred from mix tank 60, as will be discussed further herein below.

In other aspects and embodiments a shutoff valve 90 operatively coupled to controller 100 may be disposed in fluid communication with mix tank 60 and mix pump 40 to prevent the flow of solution 3 from pump 40 into mix tank 60. Additionally, in further aspects and embodiments a three-way drain/transfer valve 94 is disposed in fluid communication with both recirculation line 64 and mix pump line 42. When shut-off valve 90 is closed and drain/transfer valve is in the "transfer" position, solution 3 is routed into recirculation line 64, thence through water supply valve 80 and into tank 60. Drain/transfer valve 90 may also be placed in a "drain" position to drain mix tank 60 and the contents of system 10 through a drain line 96 by operation of pump 40.

In some aspects and embodiments the system 10 may include a pressure sensor 140 provided in fluid communication with mix tank 60, having an output 142 operatively coupled to an input 102 of controller 100, said output being representative of the pressure of the solution being mixed in tank 60 at the point where the sensor is disposed. In some embodiments pressure sensor 140 is disposed proximate a bottom surface of mix tank 60, so that the pressure sensor 140 detects the pressure of a column of water within tank 60. Sensor 140 input 102 to controller 100 may then continuously or periodically monitor solution 3 pressure, which thereby provides an accurate indication of whether sufficient powder 1 and water 2 have been added to mix tank 60 to produce a predetermined solution concentration for a given volume of fluid supplied. In some exemplary embodiments a hydrostatic pressure sensor 140 may be employed to monitor solution 3 pressure, although a wide variety of pressure sensors may be used without departing from the scope of the invention. In some aspects and embodiments pressure sensor 140 output 142 is converted by controller 100 to a specific gravity indication based upon the constituent powder 1 ingredients and the fluid 2 supplied for a given batch. In these embodiments pressure is readily converted to specific gravity so that controller 100 can readily verify that a specified batch of solution 3 is properly mixed to the correct concentration.

In some exemplary embodiments system 10 may be used to produce acid concentrate solutions for use in hemodialysis machines. In these aspects a dry acid concentrate powder 1 is typically mixed with purified water 2 to produce the desired concentrate solution. Often a batch of dry acid concentrate powder is purchased or otherwise obtained in a box or case containing, in some embodiments, two blend bags of acid powder and one bag of dextrose. In some embodiments a box or case may contain two blend bags of acid powder, one bag of dextrose, and one bag of a citric acid type powder concentrate, such as Citrasate. In either embodiment the case or box may include a bar code containing manufacturer and batch information that is scanned into controller 100 by a user using scanner 130 prior to being opened to verify the batch number and other manufacturer information. This feature of the invention is desirable for medical system products. Each bag of dry powder 1 within the case also includes a bar code, each of which is also scanned by a user using bar code scanner 130 when the bag is loaded into hopper 20 so that all bags in a batch are accounted for during the mixing process. Controller 100 is provided with specific instructions to prohibit transfer of solution 3 to a final use tank or storage tank where each bag in a batch has not been scanned by system 10. All data scanned into controller 100 is stored for purposes of verifying each batch of solution 3 mixed by system 10.

In some further aspects and embodiments output signal 142 from pressure sensor 140 is monitored by controller 100 throughout the mixing process. When each bag of powder 1 is scanned and placed in hopper 20, controller 100 begins filling mix tank 60 with a predetermined volume of fluid 2, in this example purified water. The controller then monitors level sensor 68 to determine when a predetermined batch volume is reached in mix tank 60, and then turns off input water valve 84. Controller 100 then also monitors pressure sensor 140 to determine the exact pressure of the solution 3 in tank 60. For a predetermined volume of solution 3 containing a predetermined volume of water 2 and dry powder 1, the hydrostatic pressure as detected by sensor 140 will be within a very narrow pressure range. Solution pressure is used by controller 100 as a proxy for solution concentration, since a solution 3 having a proper concentration will be at a specific pressure for a given volume of solution 3. Controller 100 confirms that the pressure range is correct for a batch of solution prior to permitting a user to transfer the batch from mix tank 60. Furthermore, when a pressure that is outside the predetermined range is detected, controller 100 provides an indication to a user through operator interface 120 of an incorrect batch. By monitoring the pressure for a predetermined batch volume, controller 100 can provide an indication of a missing powder bag, and further can prompt the operator that the missing bag was dextrose, dry acid blend, or Citrisate simply by noting the differences in pressure.

Additionally, and in further embodiments, where controller 100 has detected via bar code scanner 130 that all powder 1 bags (or cases etc.) have been placed in hopper 20 and pumped into mix tank 60, controller 100 may monitor solution 3 pressure via pressure sensor 140 output 142. Where solution 3 pressure for a predetermined volume is out of a predetermined range, controller 100 may actuate water supply 2 inlet valve 80 to provide additional fluid 2 to tank 60. In this embodiment, the inlet valve 80 is only actuated to provide additional water 2 when solution 3 pressure indicates the concentration of solution 3 is too high.

In further aspects and embodiments, controller 100 may monitor pressure sensor 140 to determine if solution 3 pressure is out of a predetermined range, either high or low, and then provide a user an indication of improper solution 3 concentration by providing a "concentration high", "concentration low", or "concentration out of range" alarm indication through user interface 120. Controller 100 may be provided with predetermined acceptable solution 3 pressure ranges for a plurality of solution 3 concentrations by volume of solution 3 mixed in tank 60. In these embodiments of the invention where an out-of-range solution 3 pressure is detected by sensor 140, the user or operator will be prompted to take corrective action, either by correcting the concentration of solution 3 or by "dumping" the mix tank 60 solution 3 by opening drain/transfer valve 90 to the drain position and operating pump 40 to remove the contents of mix tank 60 through drain 96.

In some alternative aspects and embodiments of the invention a conductivity sensor 160 may be provided in place of pressure sensor 140, said sensor 160 being disposed in the mix tank 60. Conductivity sensor 160 includes an output that is operatively coupled to an input 102 of controller 100 that provides a signal representative of the conductivity of the solution 3 in tank 60. This conductivity measurement is accordingly treated as a proxy for solution 3 concentration, and thus by continuously monitoring the conductivity of solution 3 controller 100 may then continuously adjust powder 1 and/or fluid 2 provided to mix tank 60 to maintain solution conductivity at a predetermined set point. In these embodiments, conductivity sensor 160 operates in an analogous fashion to pressure sensor 140. Controller 100 is provided with predetermined conductivity ranges for solution 3 concentrations by volume of solution 3 mixed in tank 60, rather than pressure ranges.

In yet further aspects of the invention the user interface 120 may provide indications of solution pressure, concentration, specific gravity, and conductivity visible to a user. Furthermore, controller 100 may be provided with instructions to provide an audible or visual alarm if the solution being mixed is outside of a predetermined range of pressure, concentration, specific gravity, or conductivity as determined by the sensors. In this case an operator or user can be prompted to take corrective action or "dump" the solution batch and mix a new batch as desired.

Figure 7:
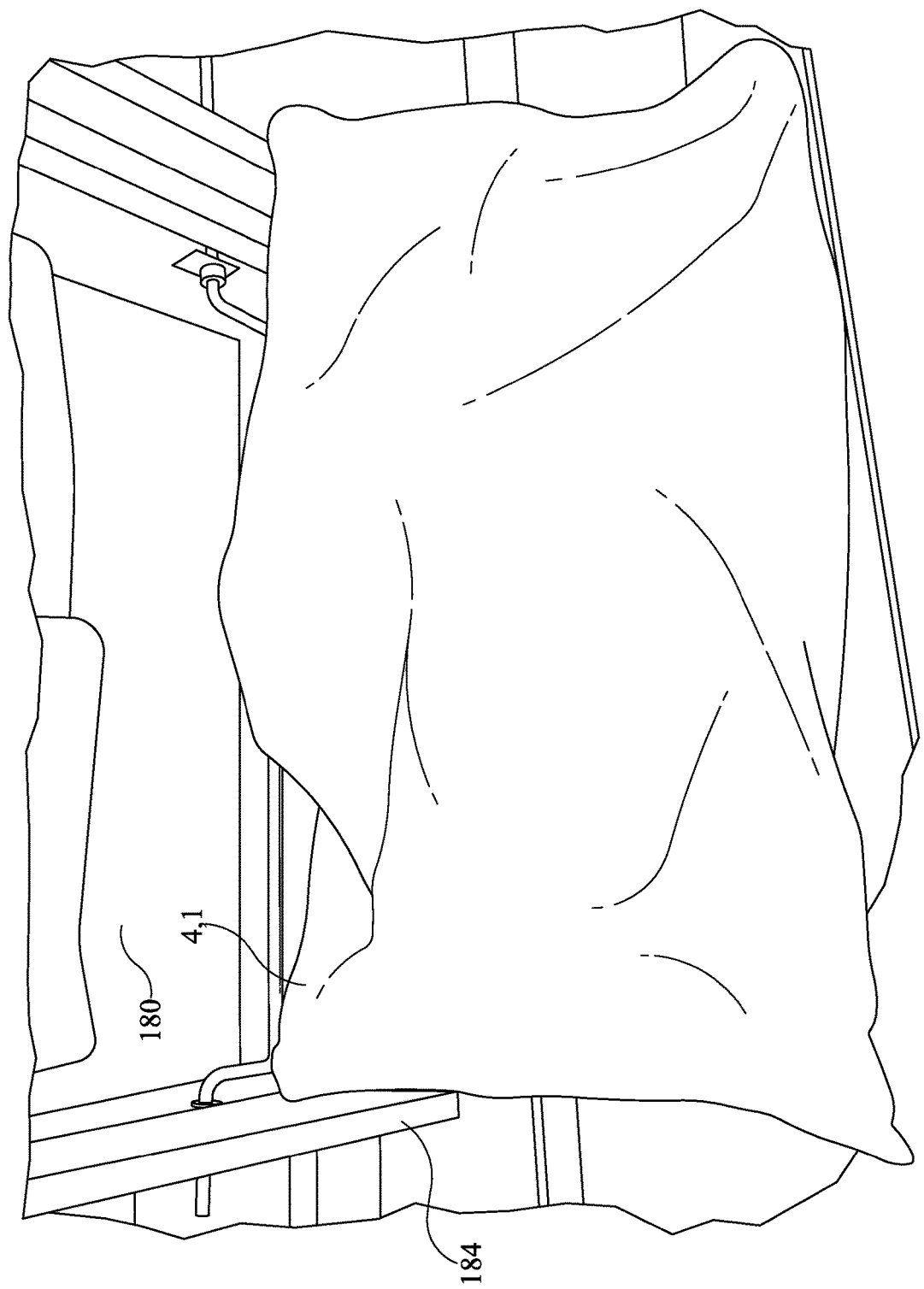
FIG. 7 illustrates an exemplary powder bag and opener for supplying a powder to a hopper in accordance with one embodiment of the present invention.

In some aspects and embodiments of the system 10 and as best seen in FIGS. 2 and 7, a bag opening system 180 may be provided, wherein a plastic powder 1 bag 4 or equivalent container of powder 1 is placed in bag 4 opening system 180 and is then automatically opened and dispensed into hopper 20. Bag opening system 180 may include a bag cutter for opening powder bags 4 and has a bottom portion 182 in fluid communication with hopper 20. In some aspects and embodiments bag opening system 180 may include a bag holder 184 that secures each powder bag 4 in a fixed position so that the bag cutter can make a consistent opening in each bag 4 and empty substantially all bag 4 contents into powder hopper 20.

In operation system 10 performs a solution 3 mixing process when a user initiates the process using interface 120 to specify what type of solution 3 is being mixed by ingredients, concentration and volume. Controller 100 begins filling mix tank 60 with fluid 2, in many cases purified water, by opening valves 80 and 84 and operating pump 40. A user or operator then scans a barcode on an acid powder 1 case (or other dry powder case) and then sequentially scans the barcodes of each powder 1 bag in the case and empties the bags into hopper 20. Controller 100 then opens powder control valve 24 to begin supplying powder through recirculation line 64 and into tank 60. Once the fluid 2 level in tank 60 is detected by level sensor 68 to be sufficient for the batch specified water supply valve 80 is shut off and pump 40 simply recirculates fluid 2 through system 10 until all powder 1 is emptied from hopper 20 into tank 60. The recirculation and mixing process then continues for a predetermined time period as provided by instructions to controller 100 to ensure complete mixing of solution 3.

Pressure sensor 140 (or alternatively conductivity sensor 160) is continuously monitored during the mixing process to ensure that the pressure (or conductivity, or specific gravity) sensed thereby is within a predetermined acceptable range for the specified solution 3 batch being mixed. Once the mix time provided by controller 100 is finished and the pressure, specific gravity, and/or conductivity is within an acceptable range, user interface 120 prompts an operator that the batch is ready to be transferred from system 10, as discussed further below. If the pressure or conductivity of solution 3 as sensed by sensors 140, 160 is out of a predetermined acceptable range, the operator is prompted to take corrective action or drain the solution 3 batch to waste through drain 96.

Figure 6:
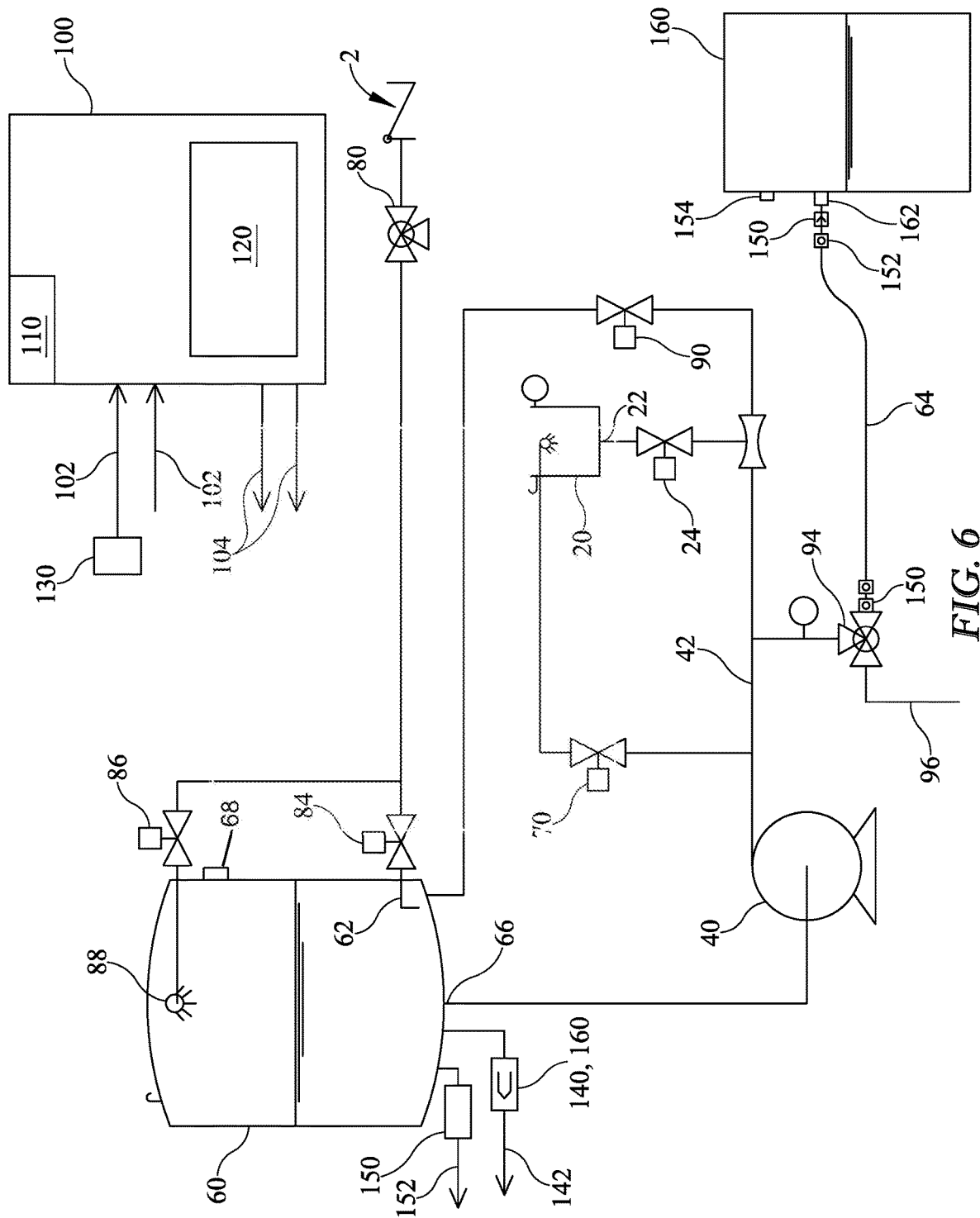
FIG. 6 illustrates an isometric diagram of a mixing system in accordance with one embodiment of the present invention.

Referring to FIGS. 1 and 6, and in accordance with various embodiments, recirculation line 64 may be provided with a coupling 150 or disconnect, or a plurality thereof, that permits it to be separated from system 10. An RFID (Radio Frequency Identification) interrogator 152 is disposed on line 64 or coupling 150 for interrogating passive RFID tags 154. Interrogator 152 is operatively coupled to controller 100 inputs 102 and outputs 104 to transfer data from a concomitant RFID tag 154. In some aspects and embodiments an RFID tag 154 is disposed on a solution storage tank 160, proximate a coupling 162 that mates with and engages coupling 150 of line 64. RFID tag 154 may include information that is unique to the type of solution 3 stored in a specific storage tank 160. In some exemplary embodiments solution 3 concentration, solution 3 formula, batch numbers, manufacturer identifiers, powder 1 expiration dataes, and mixing dates may be stored as pertinent data in RFID tag 154. Any data desired to track and verify proper preparation and supply chain information may be stored in RFID tag 154 without departing from the scope of the invention.

In operation, when solution 3 mix process is completed, recirculation line 64 is decoupled from system 10 and coupled to storage tank 160. RFID interrogator 152 is then disposed proximate RFID tag 154, and reads the data stored in the RFID tag 154 and supplies the tag 154 data to controller 100, to verify that the type of solution 3 in mix tank 60 is the same as that being stored in storage tank 160. Where controller 100 determines that the solution 3 in mix tank 60 and storage tank 160 are the same, it permits the transfer of solution 3 by operation of mix pump 40. A user input transfer button or indication may be provided via operator interface 120 to facilitate the operation. Where controller 100 determines that the solution 3 in mix tank 60 and storage tank 160 are not the same, operator interface 120 provides an audible and/or visual alarm to a user and prohibits the transfer of solution 3 into storage tank 160 until the user resolves the mismatch. This feature of the invention prohibits the transfer of incorrect solution 3 batches into a storage tank 160 and is thus useful for medical applications such as hemodialysis where acid solutions 3 must be produced and stored in very specific concentrations for use. Once solution 3 is properly transferred to storage tank 160 and mix tank 60 is completely evacuated, controller 100 shuts off pump 40 and provides an indication to a user that the transfer process is complete. The user is then free to re-couple line 64 into system 10, and begin a new solution 3 batch.

Once the batch mixing and transfer processes are complete, and in accordance with some aspects and embodiments, controller 100 may initiate a rinse process to clean system 10 after batch transfer. In these embodiments fluid 1 is provided through controller 100 operating rinse valve 86 and spray head 88 for a specified time period or volume. Pump 40 may be run to circulate rinse fluid 1 through system 10. Once the rinse cycle is completed controller 100 removes the rinse fluid 1 by operation of pump 40 through drain 96. In some alternative embodiments a user or operator may manually initiate and control the rinse cycle through operator interface 120.

The term "processor" or alternatively "controller" is used herein generally to describe various apparatus relating to the operation of one or more light sources. A controller can be implemented in numerous ways (e.g., such as with dedicated hardware) to perform various functions discussed herein. A "processor" is one example of a controller which employs one or more microprocessors that may be programmed using software (e.g., microcode or machine instructions) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present disclosure discussed herein. The terms "program" or "computer program" are used herein in a generic sense to refer to any type of computer code (e.g., software or microcode) that can be employed to program one or more processors or controllers.

The term "user interface" as used herein refers to an interface between a user or operator and one or more devices that enables interaction between the user and the device(s). Examples of user interfaces that may be employed in various implementations of the present disclosure include, but are not limited to, switches, potentiometers, buttons, dials, sliders, a mouse, keyboards, keypads, various types of game controllers (e.g., joysticks), track balls, display screens, various types of graphical user interfaces (GUIs), smartphones, watches, tablets, personal computing platforms, touch screens, microphones and other types of sensors that may receive some form of human-generated stimulus and generate a signal in response thereto.

The terms "valve" or "control valve" used herein may refer to any device used to regulate the flow of fluid through a line or system. The valves referred to in the various embodiments can be actuated electrically or hydraulically, and may include analog or digital position feedback outputs operatively coupled to controller inputs that are indicative of valve position. Additionally, valves may be multiple position valves, e.g. two, three or four-way valves as necessary without departing from the scope of the invention.

The foregoing detailed description of the embodiments of the invention is presented primarily for clearness of understanding and no unnecessary limitations are to be understood or implied therefrom. Modifications to the present invention in its various embodiments will become obvious to those skilled in the art upon reading this disclosure and may be made without departing from scope of the invention and the claims appended hereto.

We claim:

1. A system for mixing a liquid with a powder into a solution batch comprising: a hopper into which said powder is deposited having a powder outlet therein; a mix tank having a liquid supply inlet, a recirculation inlet, and a solution outlet; a sensor in fluid communication with said mix tank for monitoring the pressure of the solution in said mix tank and determining the specific gravity of said solution; and a mix pump in fluid communication with said solution outlet, said powder outlet, and said recirculation inlet.

2. The system as claimed in claim 1 comprising: a controller having a data memory and a plurality of inputs and outputs for supplying and receiving signals, and an operator interface operatively coupled to said controller for receiving user commands.

3. The system as claimed in claim 2 comprising; a bar code scanner operatively coupled to an input of said controller for inputting data related to said batch.

4. The system of claim 3 comprising: a recirculation and transfer hose in fluid communication with said mix pump and said recirculation inlet, said transfer hose having a coupling thereon for disconnecting said transfer hose from said recirculation inlet; an RFID interrogator disposed on said transfer hose having an input operatively coupled to said controller; and whereby said controller monitors data provided by said RFID interrogator to prohibit said mix pump from operating to transfer said solution through said transfer hose when said interrogator does not read specified data from interrogation of a remote RFID tag.

5. The system of claim 1 wherein said sensor comprises: a pressure sensor disposed in fluid communication with said mix tank for monitoring the pressure of the solution in said mix tank to determine whether sufficient powder has been added to a predetermined liquid volume to produce a predetermined solution concentration.

6. The system of claim 2 comprising: a pressure sensor disposed in fluid communication with said mix tank for monitoring the pressure of the solution in said system having an output operatively coupled to an input of said controller, whereby said controller provides an indication of solution concentration through said operator interface.

7. The system of claim 6 comprising: an alarm provided through said operator interface when said solution concentration is outside of a predetermined range as determined by said pressure sensor.

8. The system of claim 7 wherein said controller determines the specific gravity of said solution batch based upon said pressure sensor output and the quantity of powder and fluid provided to said mix tank.

9. A system for mixing a liquid and a powder into a solution batch comprising: a hopper into which said powder is deposited having a powder outlet therein and a powder control valve in fluid communication with said powder outlet; a mix tank having a liquid supply inlet in fluid communication with a liquid inlet valve, a recirculation inlet in fluid communication with said liquid inlet valve, and a solution outlet; a mix pump in fluid communication with said solution outlet, said powder outlet, and said recirculation inlet; a controller having a data memory and a plurality of inputs and outputs for supplying and receiving signals, and an operator interface operatively coupled to said controller for receiving user commands; and a pressure sensor disposed in fluid communication with said mix tank for monitoring the pressure of the solution in said system, said pressure sensor having an output operatively coupled to an input of said controller, whereby said controller provides an indication of solution concentration through said operator interface.

10. The system of claim 9 comprising: a bar code scanner operatively coupled to an input of said controller for inputting data related to said batch.

11. The system of claim 10 comprising: a set of instructions provided to said controller whereby said bar code scanner reads bar code data provided on each container of powder supplied to said hopper for a specified solution batch, and wherein said controller provides an indication through said operator interface when said specified solution batch is missing a container of powder.

12. The system of claim 11 wherein said powder is provided in a plurality of preselected container each having data identification thereon comprising: a set of instructions provided to said controller whereby said bar code scanner reads data provided on each container of powder supplied to said hopper for a specified solution batch, and wherein said controller provides an indication through said operator interface when said specified solution batch is missing a container of powder.

13. The system of claim 11 comprising: a recirculation and transfer hose in fluid communication with said mix pump and said recirculation inlet, said transfer hose having a coupling thereon for disconnecting said transfer hose from said recirculation inlet; an RFID interrogator disposed on said transfer hose having an input operatively coupled to said controller; and Page 5 of 10 whereby said controller monitors data provided by said RFID interrogator to prohibit said mix pump from operating to transfer said solution through said transfer hose when said interrogator does not read specified data from interrogation of a remote RFID tag.

14. The system of claim 10 wherein said controller monitors said pressure sensor and provides an indication through said operator interface that the pressure of said solution batch is out of a predetermined pressure range.

15. The system of claim 14 wherein said controller converts said pressure sensor output to a specific gravity measure for a specified solution batch.

16. The system of claim 10 comprising: a conductivity sensor disposed in fluid communication with said mix tank for monitoring the conductivity of the solution in said system, said conductivity sensor having an output operatively coupled to an input of said controller, whereby said controller provides an indication of solution concentration through said operator interface.

17. A method for mixing a liquid and a powder into a solution batch comprising: providing a hopper into which said powder is deposited having a powder outlet therein and a powder control valve in fluid communication with said powder outlet; providing a mix tank having a liquid supply inlet in fluid communication with a liquid inlet valve, a recirculation inlet in fluid communication with said liquid inlet valve, and a solution outlet; providing a mix pump in fluid communication with said solution outlet, said powder outlet, and said recirculation inlet; providing a controller having a data memory and an instruction set for operation, said controller having a plurality of inputs and outputs for supplying and receiving signals, and an operator interface operatively coupled to said controller for receiving user commands; and providing a pressure sensor disposed in fluid communication with said mix tank for monitoring the pressure of the solution in said system, said pressure sensor having an output operatively coupled to an input of said controller, whereby said controller provides an indication of solution concentration through said operator interface.

18. The method of claim 17 further comprising: monitoring said pressure sensor output to determine whether there is an out of range solution pressure for a specified solution batch, and providing an indication through said operator interface of a missing quantity of powder based said determination.

19. The method of claim 17 further comprising: providing a bar code scanner operatively coupled to an input of said controller for inputting data related to said solution batch and storing said data for future verification.

* * * * *